US012414697B2

(12) United States Patent
Chen et al.

(10) Patent No.: US 12,414,697 B2
(45) Date of Patent: Sep. 16, 2025

(54) SINGLE-ARM TWO-ELECTRODE BLOOD PRESSURE MEASURING DEVICE AND MEASURING METHOD THEREOF

(71) Applicants: Mei-Fen Chen, Taoyuan (TW);
Wen-Chen Lin, Taoyuan (TW);
Wen-Chi Lin, Taoyuan (TW);
Shao-Hung Lu, Taipei (TW);
Yung-Hsin Chen, Taoyuan (TW)

(72) Inventors: Mei-Fen Chen, Taoyuan (TW);
Wen-Chen Lin, Taoyuan (TW);
Wen-Chi Lin, Taoyuan (TW);
Shao-Hung Lu, Taipei (TW);
Yung-Hsin Chen, Taoyuan (TW)

( * ) Notice: Subject to any disclaimer, the term of this patent is extended or adjusted under 35 U.S.C. 154(b) by 452 days.

(21) Appl. No.: 17/874,331

(22) Filed: Jul. 27, 2022

(65) Prior Publication Data
US 2023/0172461 A1    Jun. 8, 2023

(30) Foreign Application Priority Data

Dec. 2, 2021    (TW) ................................ 110144969

(51) Int. Cl.
*A61B 5/021*    (2006.01)
*A61B 5/00*    (2006.01)
(Continued)

(52) U.S. Cl.
CPC .......... *A61B 5/02125* (2013.01); *A61B 5/308* (2021.01); *A61B 5/33* (2021.01);
(Continued)

(58) Field of Classification Search
None
See application file for complete search history.

(56) References Cited

U.S. PATENT DOCUMENTS 5,333,615 A * 8/1994 Craelius ................. A61B 5/335
600/509
9,307,915 B2    4/2016 McCombie et al.
(Continued)

FOREIGN PATENT DOCUMENTS

CN    105988584    2/2019
TW    201726051    8/2017
(Continued)

*Primary Examiner* — Mallika D Fairchild
(74) *Attorney, Agent, or Firm* — JCIPRNET

(57) ABSTRACT

A single-arm two-electrode blood pressure measuring device and a measuring method thereof are provided. The single-arm two-electrode blood pressure measuring device includes two sensing electrodes, a photoplethysmogram (PPG) sensor, an analog signal processing unit, a filter and amplifier unit, an analog-to-digital conversion unit, and a digital signal processing unit. The single-arm two-electrode blood pressure measuring method includes: providing the two sensing electrode to sense an electrocardiography (ECG) signal of an user; providing the PPG sensor to sense a PPG signal; inverting a common mode signal between the two sensing electrodes and outputting to a filter of the analog signal processing unit by a differential amplifier; filtering and amplifying the ECG signal and the PPG signal by the filter and amplifier unit; and detecting multiple feature points of the ECG signal and the PPG signal to generate an estimated blood pressure value by the digital signal processing unit.

17 Claims, 10 Drawing Sheets

(51) Int. Cl.
 *A61B 5/308* (2021.01)
 *A61B 5/33* (2021.01)
(52) U.S. Cl.
 CPC .......... *A61B 5/6824* (2013.01); *A61B 5/6831* (2013.01); *A61B 5/7225* (2013.01)

(56) References Cited

U.S. PATENT DOCUMENTS

| | | |
|---|---|---|
| 10,258,288 B2 | 4/2019 | Penders et al. |
| 2008/0200823 A1* | 8/2008 | Cho .................. A61B 5/02055 600/521 |
| 2014/0073862 A1* | 3/2014 | Rodriguez-Llorente .................... A61B 5/7275 600/301 |
| 2015/0164404 A1* | 6/2015 | Euliano .............. A61B 5/02416 600/301 |
| 2017/0215749 A1* | 8/2017 | Zhuo .................. A61B 5/02055 |
| 2019/0090760 A1 | 3/2019 | Kinast et al. |
| 2020/0312453 A1* | 10/2020 | Räisänen ................ G06F 3/016 |
| 2020/0397318 A1* | 12/2020 | Kawabata ............... A61B 5/352 |

FOREIGN PATENT DOCUMENTS

| | | |
|---|---|---|
| TW | I675643 | 11/2019 |
| TW | I716138 | 1/2021 |

* cited by examiner

SINGLE-ARM TWO-ELECTRODE BLOOD PRESSURE MEASURING DEVICE AND MEASURING METHOD THEREOF

CROSS-REFERENCE TO RELATED APPLICATION

This application claims the priority benefit of Taiwan application serial no. 110144969, filed on Dec. 2, 2021. The entirety of the above-mentioned patent application is hereby incorporated by reference herein and made a part of this specification.

BACKGROUND

Technical Field

The disclosure relates to a blood pressure measuring device and a measuring method thereof, and particularly relates to a single-arm two-electrode blood pressure measuring device and a measuring method thereof that can continuously measure blood pressure.

Description of Related Art

Blood pressure is one of the important physiological parameters and is an indicator that needs to be monitored frequently especially for patients with cardiovascular disease. Cardiovascular patients or the elderly must always detect and record blood pressure values, but the existing household sphygmomanometers mainly use the oscillometry principle, which requires the use of a blood pressure cuff to temporarily compress the blood vessels, and cannot achieve the objective of automatic and continuous blood pressure monitoring. In order to improve the comfort of blood pressure measurement and meet the demand for long-term measurement, many researches have discussed the relationship between the time difference between blood delivery from the heart to the peripheral blood vessels and the blood pressure, which is the so-called pulse wave transit time (PWTT) principle. The theory of such method is mainly based on the fact that the time taken for a blood pressure wave to be transmitted between two parts of an artery is inversely proportional to the blood pressure, that is, when the blood pressure rises, the PWTT between two endpoints decreases, and vice versa. The most common way to estimate the PWTT is to use a photoplethysmography (PPG) and an electrocardiography (ECG) as the basis to detect changes in waveform features of ECG and PPG signals of each individual, thereby calculating the blood pressure level.

There are many wearable devices on the market that use the PWTT principle to calculate the blood pressure, such as a smart blood pressure watch. However, based on the limitation of the measurement principle, for the smart blood pressure watch that detects the ECG signal as the basis for calculating heart contraction, the hand that is not wearing the watch is required to touch an electrode (for example, a crown) on the watch when in use to obtain the ECG signal, thereby calculating the blood pressure, so the function of continuous blood pressure measurement is not possible. In order to achieve the function of continuous blood pressure detection, there are also many researches and patents that implement the objective of continuous blood pressure measurement based on the integration of existing ECG and PPG technologies in conjunction with algorithms (for example, U.S. Pat. No. 9,307,915 and U.S. Patent No. 2019/0090760). However, due to the limitation of the need to obtain clear ECG waveforms, the researches or devices are usually based on three-electrode ECG measurement technology, so more wires are required to connect the electrodes, which is a problem for long-term use.

SUMMARY

The disclosure provides a single-arm two-electrode blood pressure measuring device and a measuring method thereof, which can achieve the objective of continuously measuring blood pressure in a single arm.

A single-arm two-electrode blood pressure measuring method of the disclosure includes the following steps. Two sensing electrodes are provided to sense an electrocardiography (ECG) signal of a user. A photoplethysmogram (PPG) sensor is provided to sense a PPG signal of the user. A common mode signal between the two sensing electrodes is inverted and output to a filter. The ECG signal and the PPG signal are filtered and amplified. Multiple feature points of the ECG signal and the PPG signal are detected to generate an estimated blood pressure value.

A single-arm two-electrode blood pressure measuring device of the disclosure includes a sensing electrode, a PPG sensor, an analog signal processing unit, an analog-to-digital conversion unit, and a digital signal processing unit. The analog signal processing unit includes a filter, a differential amplifier, and a filter and amplifier unit. In the disclosure, the number of sensing electrodes is two, which are configured to be placed on an upper arm portion of a user to obtain an ECG signal of the user. The PPG sensor is configured to be placed on the upper arm portion of the user to sense a PPG signal of the user. The filter removes noise according to a reference voltage. The differential amplifier is coupled to the filter, and inverts a common mode signal between the two sensing electrodes and then outputs to the filter. Accordingly, the inverted common mode signal serves as the reference voltage of the filter. The analog-to-digital conversion unit is coupled to the analog signal processing unit and is configured to convert the ECG signal and the PPG signal from an analog format to a digital format. The digital signal processing unit is coupled to the analog-to-digital conversion unit and includes a processor. The processor is configured to detect multiple feature points of the ECG signal and the PPG signal to generate an estimated blood pressure value.

Based on the above, in the single-arm two-electrode blood pressure measuring device of the disclosure, the common mode signal in the ECG signal is invert amplified to serve as the reference voltage of the filter, thereby suppressing noise to achieve the objective of measuring EEG in a single arm with two electrodes, and in conjunction with the acquisition of the PPG signal and the analysis of feature points based on pulse wave transit time, the objective of continuous blood pressure monitoring is implemented.

DETAILED DESCRIPTION OF DISCLOSED EMBODIMENTS

Figure 1:
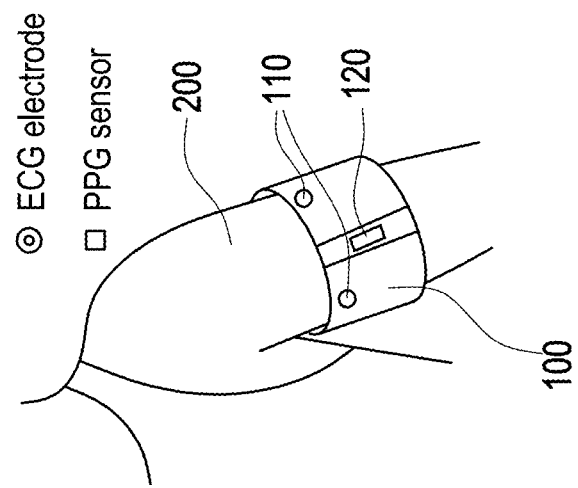
FIG. 1 is a schematic diagram of use of a single-arm two-electrode blood pressure measuring device according to an embodiment of the disclosure.
Figure 2:
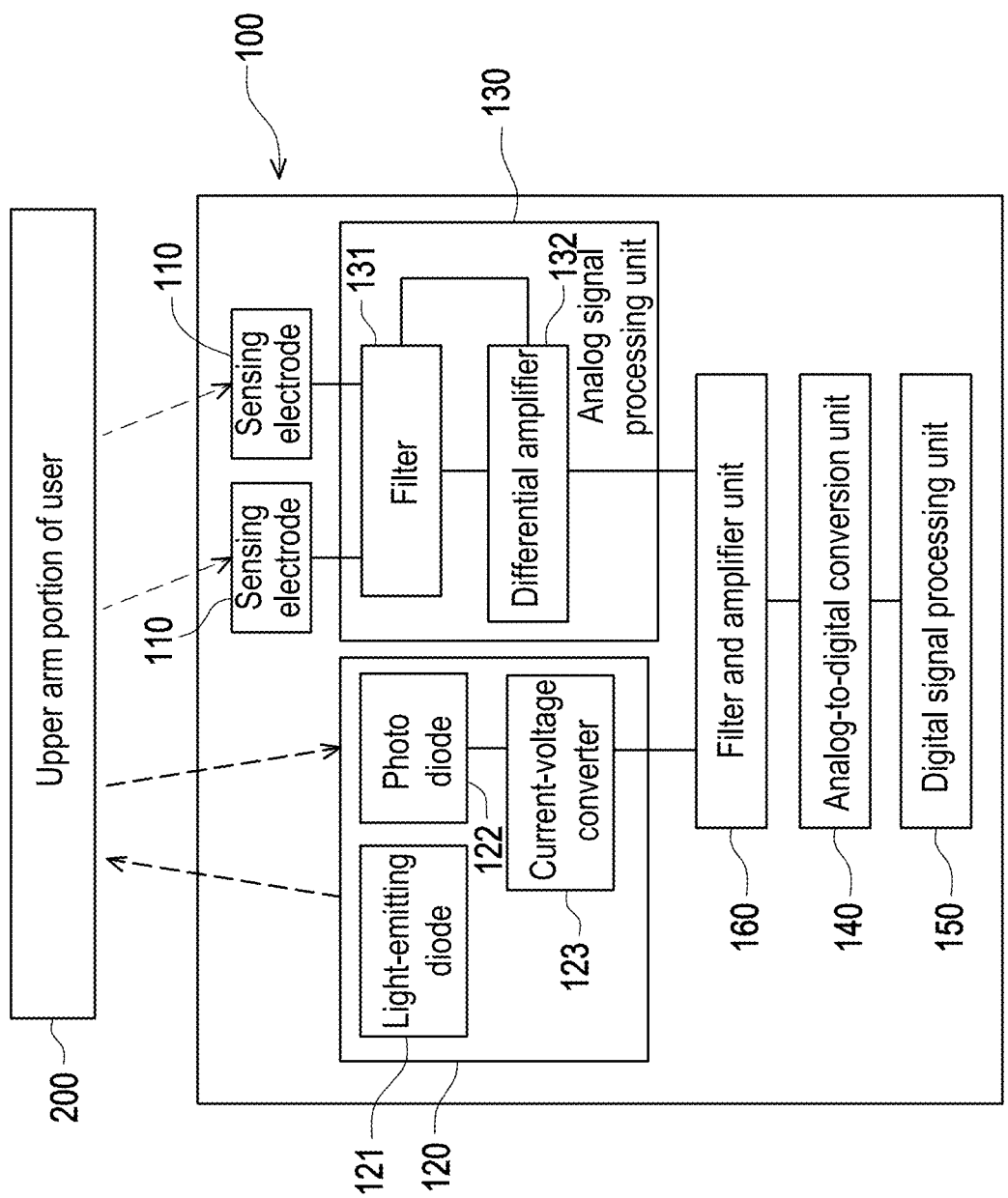
FIG. 2 is a block diagram of a single-arm two-electrode blood pressure measuring device according to an embodiment of the disclosure.

FIG. 1 is a schematic diagram of use of a single-arm two-electrode blood pressure measuring device 100 according to an embodiment of the disclosure. FIG. 2 is a block diagram of a single-arm two-electrode blood pressure measuring device according to an embodiment of the disclosure. The single-arm two-electrode blood pressure measuring device 100 includes two sensing electrodes 110, a photoplethysmogram (PPG) sensor 120, an analog signal processing unit 130, a filter and amplifier unit 160, an analog-to-digital conversion unit 140, and a digital signal processing unit 150. The sensing electrode 110 is configured to be placed on an upper arm portion 200 of a user to obtain an electrocardiography (ECG) signal of the user. The PPG sensor 120 is configured to contact the upper arm portion 200 of the user to sense a PPG signal of the user. The analog signal processing unit 130 includes a filter 131 and a differential amplifier 132. The filter 131 is coupled to the two sensing electrodes 110 and transmits a measured signal to the differential amplifier 132. Since the ECG signal of an arm portion is weak, the removal of noise becomes a very important task. A noise signal may also be referred to as a common mode signal in terms of circuit design. In the disclosure, the differential amplifier 132 is used to invert the common mode signal between the sensing electrodes 110 and then output to the filter 131 as a reference voltage to reduce the influence of noise using the concept of noise cancellation. Then, the filter and amplifier unit 160 is used to further filter and amplify the measured ECG signal and PPG signal, and the ECG signal and the PPG signal are converted from an analog format to a digital format by the analog-to-digital conversion unit 140 to be transmitted to the digital signal processing unit 150 for processing and to calculate multiple feature parameters of the ECG signal and the PPG signal to generate an estimated blood pressure value of the user.

Figure 3:
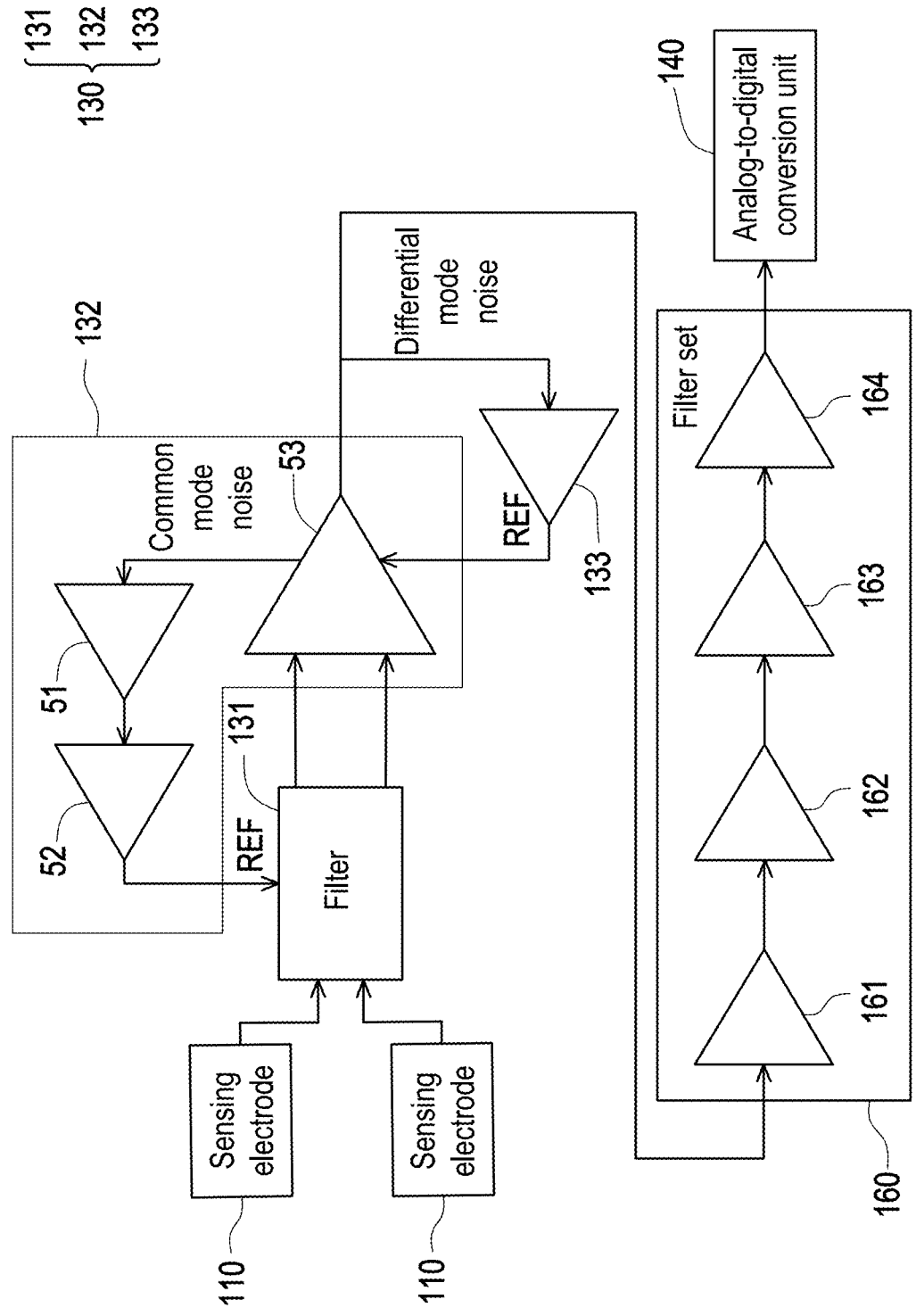
FIG. 3 is a block diagram of a sensing electrode, an analog signal processing unit, an analog-to-digital conversion unit, and a filter and amplifier unit according to an embodiment of the disclosure.
Figure 4:
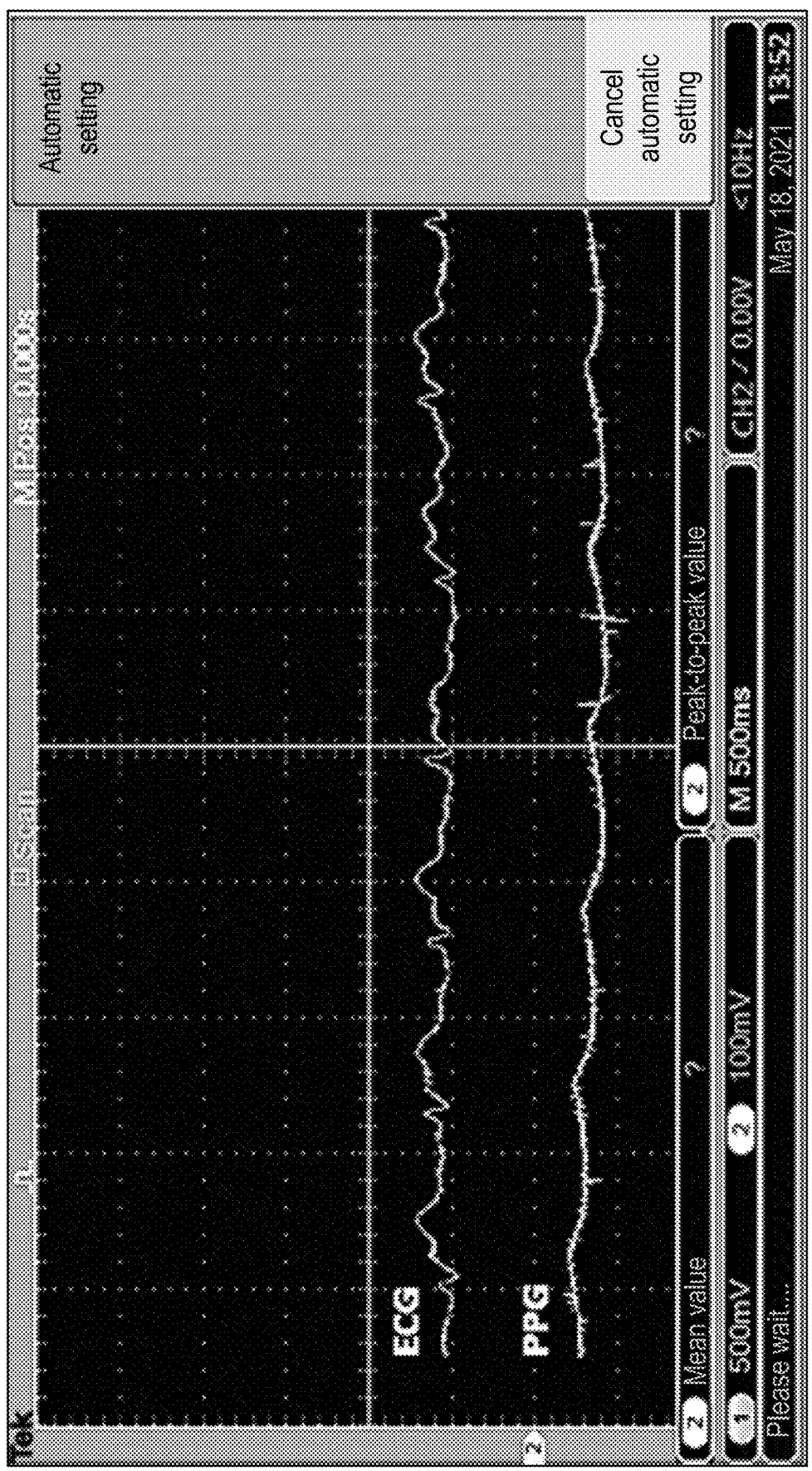
FIG. 4 is waveforms of an electrocardiography (ECG) signal and a photoplethysmography (PPG) signal on an upper arm portion of a user actually measured by a single-arm two-electrode blood pressure measuring device of the disclosure as displayed by an oscilloscope.

FIG. 3 is a block diagram of the sensing electrode 110, the analog signal processing unit 130, the analog-to-digital conversion unit 140, and the filter and amplifier unit 160 according to an embodiment of the disclosure. In the embodiment, the differential amplifier 132 includes a buffer 51, an inverting amplifier 52, and an instrumentation amplifier 53. Specifically, the buffer 51 is coupled to a common mode output pin of the instrumentation amplifier 53 and is configured to input the common mode signal to the filter 131 by the inverting amplifier 52 to serve as the reference voltage for noise cancellation. An output terminal of the instrumentation amplifier 53 has a differential mode signal, which is the ECG signal to be obtained by the disclosure. After passing through an integrator 133, the differential mode signal is also input to the instrumentation amplifier 53 as a reference voltage for removing direct current offset. In an embodiment, the buffer 51 is at least one voltage follower, and the integrator 133 may be a differential mode suppressor. In order to obtain a signal with better quality, the filter and amplifier unit 160 may be a series of filter combinations, such as a band pass filter 161, a first low pass filter 162, an offset adjuster 163, and a second low pass filter 164 coupled in sequence. FIG. 4 is waveforms of an ECG signal and a PPG signal on an upper arm portion of a user actually measured by a single-arm two-electrode blood pressure measuring device of the disclosure as displayed by an oscilloscope.

Figure 5:
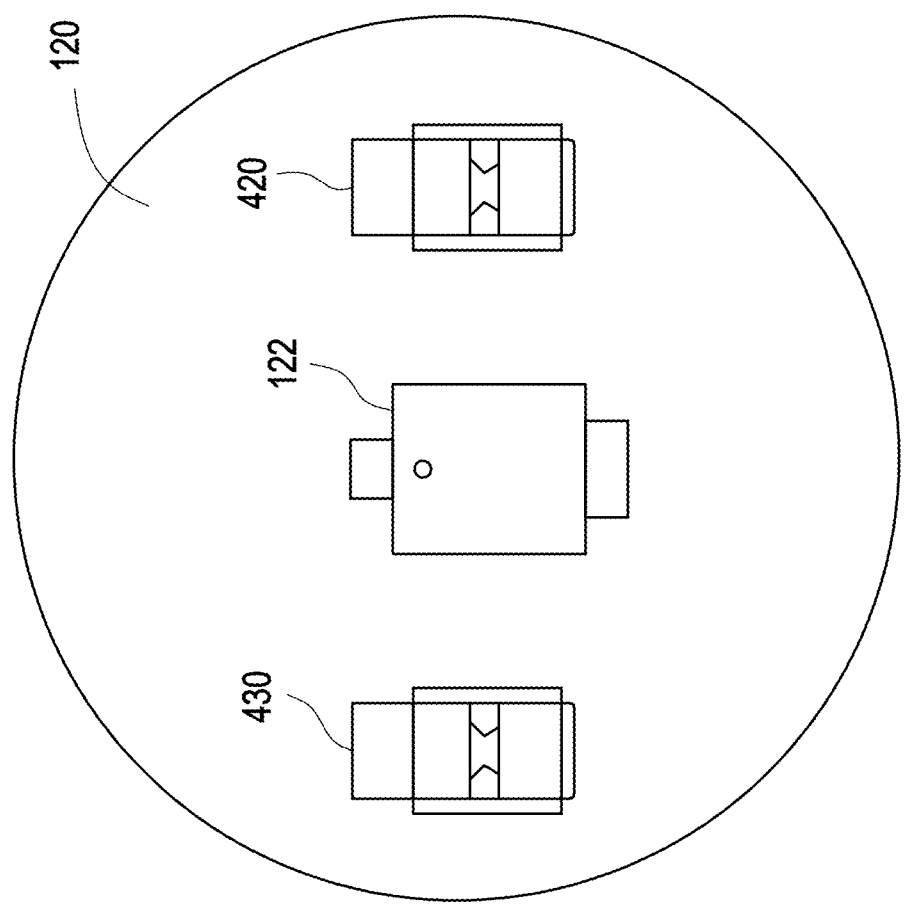
FIG. 5 is a schematic diagram of a PPG sensor according to an embodiment of the disclosure.

FIG. 5 is a schematic diagram of a PPG sensor according to an embodiment of the disclosure. In the embodiment, the PPG sensor 120 includes a photo diode 122 and two light-emitting diodes (LEDs) (420 and 430), wherein the LEDs (420 and 430) may be green LEDs or red LEDs and are configured to emit light into human tissues, and the photo diode 122 is configured to absorb light reflected by the human tissues and convert into electrical signals to represent changes in blood volume, that is, the PPG signal, in the human tissues.

Figure 6:
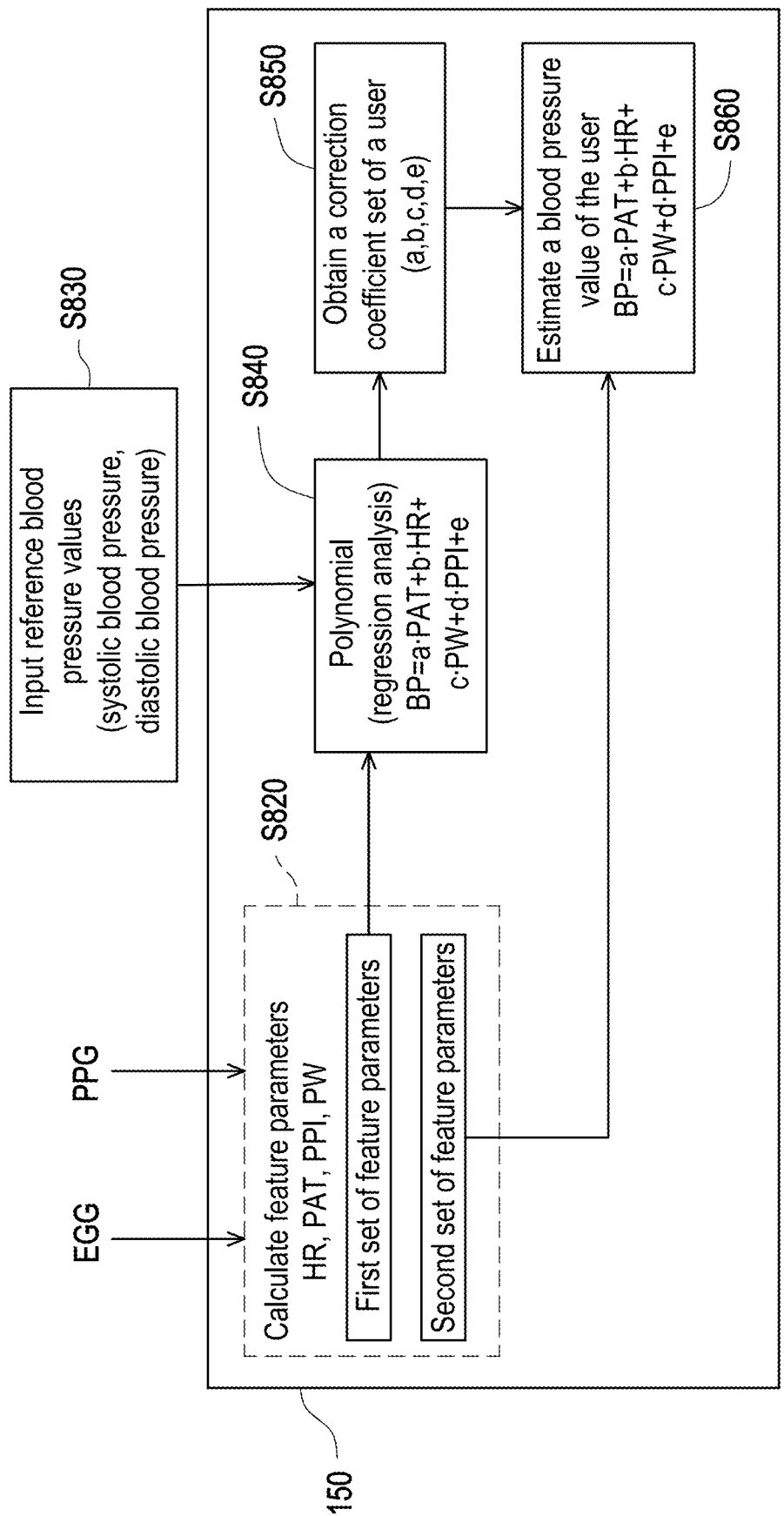
FIG. 6 is a flowchart of blood pressure estimation according to an embodiment of the disclosure.
Figure 7:
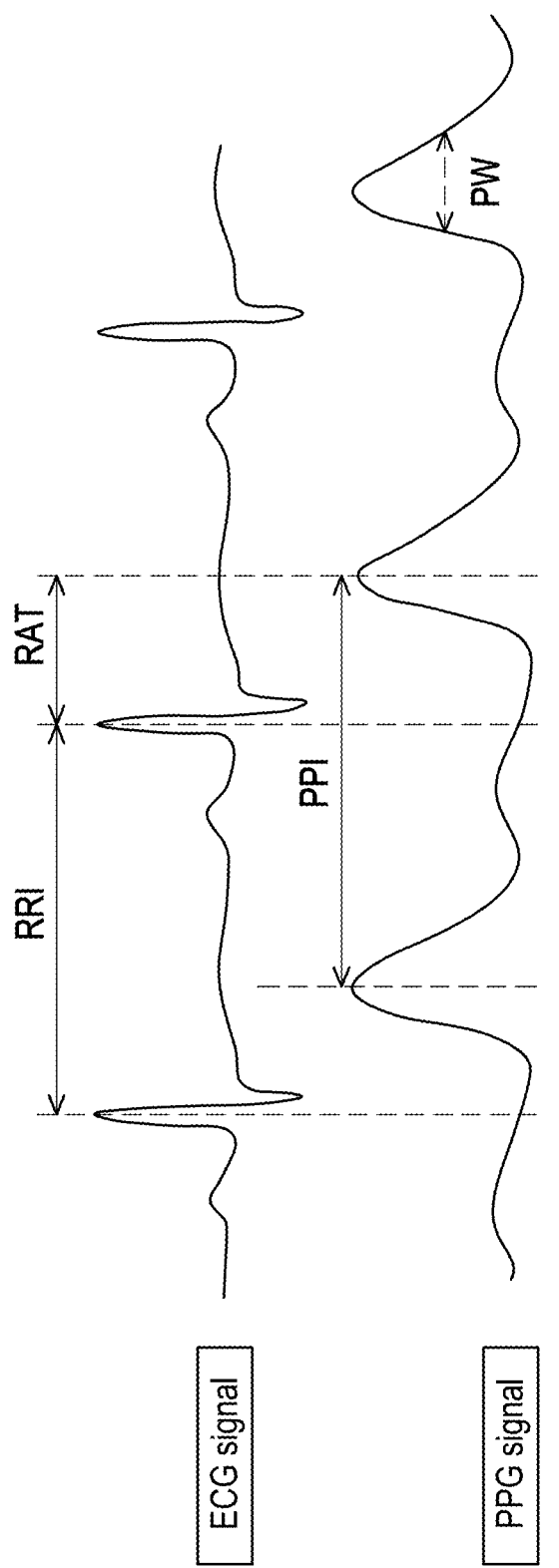
FIG. 7 is a schematic diagram of feature parameters of waveforms of an ECG signal and a PPG signal according to an embodiment of the disclosure.

Next, a blood pressure estimation process of the disclosure will be described. FIG. 6 is a flowchart of blood pressure estimation according to an embodiment of the disclosure. As shown in FIG. 6, when the ECG signal and the PPG signal enter the digital processing unit 150, the processing and calculation of blood pressure estimation may be performed by a calculation model built on the digital processing unit 150. The first processing procedure of the calculation model is Step S820, which is to calculate the feature parameters of the ECG signal and the PPG signal. The feature parameters may include a heart rate (HR), a pulse arrival time (PAT), a pulse-to-pulse interval (PPI), and a pulse width (PW). FIG. 7 is a schematic diagram of feature parameters of waveforms of an ECG signal and a PPG signal according to an embodiment of the disclosure. The definitions of the feature parameters are explained as follows:

Heart rate: the number of heart beats per minute, that is, 60/RRI, indicated as HR;

Pulse arrival time: the time difference between an R wave and a peak value of a pulse wave, indicated as PAT;

Pulse-to-pulse interval: the time interval between the peak values of the pulse wave, indicated as PPI;

Pulse width: the time interval between when a waveform of the pulse wave rises to half an amplitude of the pulse wave and when the waveform drops to half the amplitude of the pulse wave, indicated as PW.

Figure 8:
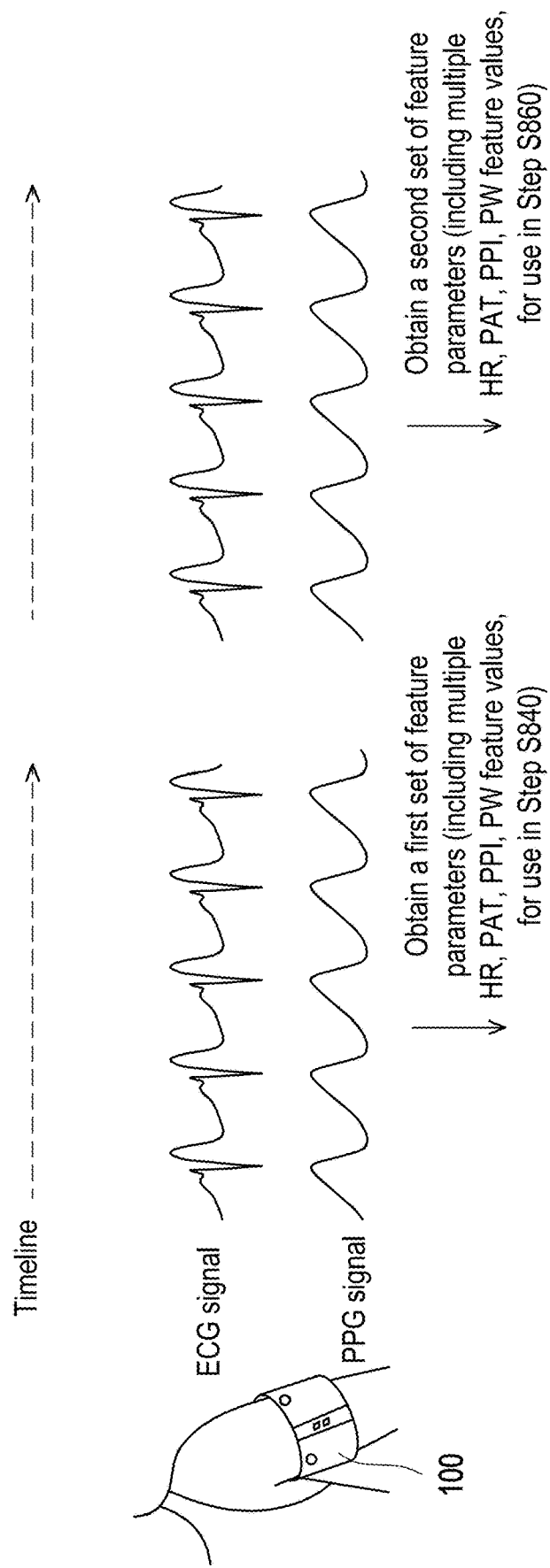
FIG. 8 is a schematic diagram of obtaining a first set of feature parameters and a second set of feature parameters according to an embodiment of the disclosure.

The disclosure adopts a linear polynomial to estimate blood pressure, wherein an equation of the embodiment is as follows:

$$\text{Blood Pressure (BP)} = a \cdot \text{PAT} + b \cdot \text{HR} + c \cdot \text{PW} + d \cdot \text{PPI} + e \quad (1),$$

where BP is the estimated blood pressure value, and a, b, c, d, and e are coefficients. The feature parameters are divided into a first set of feature parameters and a second set of feature parameters. FIG. 8 is a schematic diagram of obtaining a first set of feature parameters and a second set of feature parameters according to an embodiment of the disclosure. For the description of the blood pressure estimation process of FIG. 6, please refer to FIG. 8 at the same time. The disclosure first uses the single-arm two-electrode blood pressure measuring device 100 to detect the ECG signal or the PPG signal for a period of time, and perform a feature parameter algorithm. Values of PAT, HR, PPI, and PW may be calculated from the waveforms of the ECG signal and the PPG signal between two heartbeats. Therefore, by detecting the ECG signal or the PPG signal for a period of time, multiple feature parameter data, which is referred to here as the first set of feature parameters, may be obtained. Next, proceed to Step S830, which is to input a reference blood pressure value (including systolic blood pressure and diastolic blood pressure) of the user. The reference blood pressure value may be obtained by the user measuring using a household sphygmomanometer or by the user inputting normal blood pressure. Next, proceed to Step S840, which is to substitute the reference blood pressure value and the first set of feature parameters into Polynomial Equation (1), and values of the coefficients a to e of each feature parameter are solved by linear regression. The set of coefficients is obtained according to the ECG signal, the PPG signal, and the reference blood pressure value of the user, and thus includes physiological signal features related to the user. In the disclosure, a to e are referred to as a correction coefficient set of the user. Next, in Step S850, the single-arm two-electrode blood pressure measuring device 100 continuously detects the ECG signal or the PPG signal, and also performs an analysis of the waveforms to obtain the values of PAT, HR, PPI, and PW, which are referred to here as the second set of feature parameters, at this time. Then, proceed to Step S860, which is to substitute the second set of feature parameters and the correction coefficient set obtained in Step S850 into Equation (1) to calculate the blood pressure of the user. In other words, the single-arm two-electrode blood pressure measuring device 100 of the disclosure obtains continuous ECG signals and PPG signals to continuously perform analysis and calculation of the waveform features of the EEG signal and the PPG signal, thereby continuously estimating the blood pressure value of the user.

Figure 9:
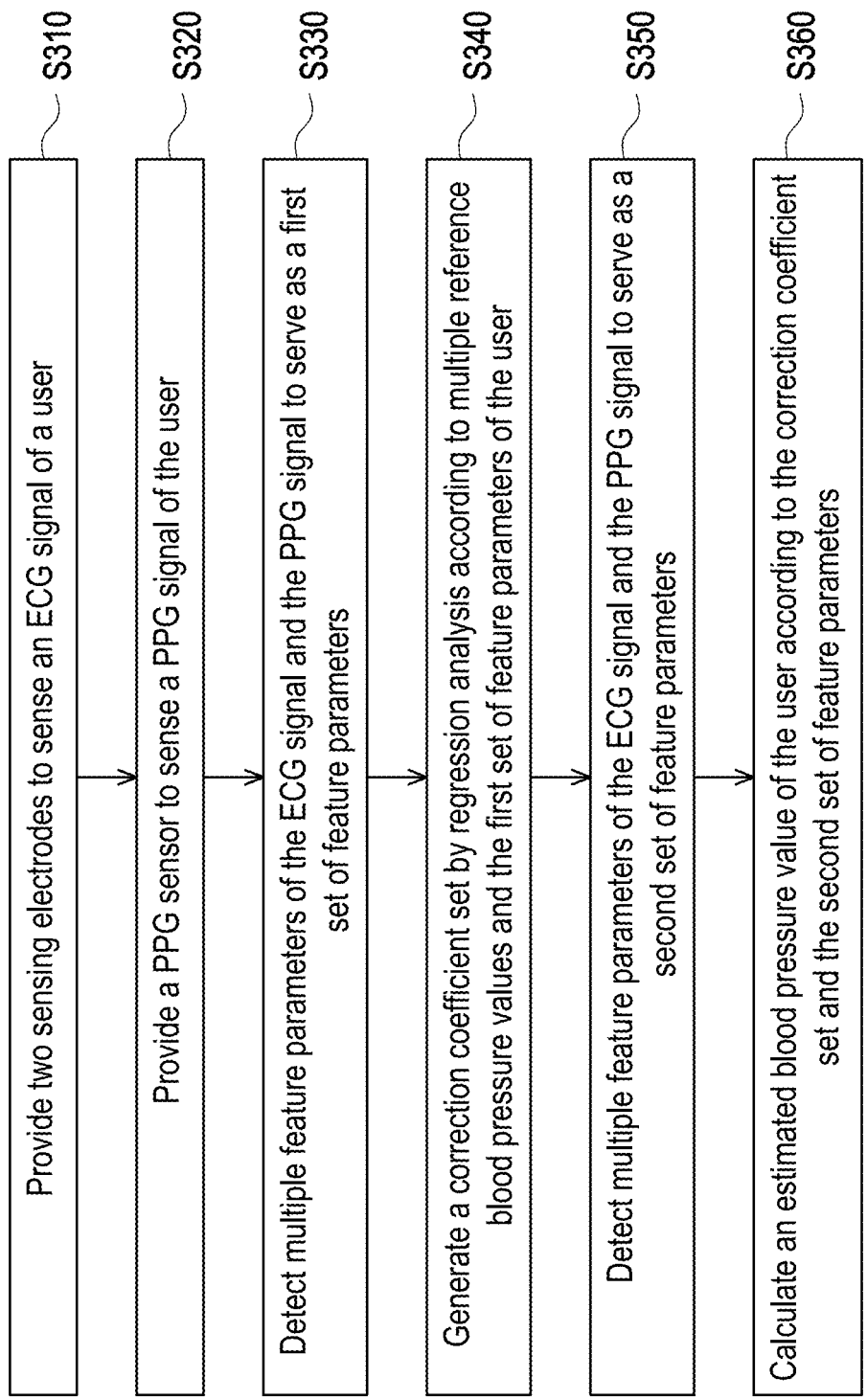
FIG. 9 is a flowchart of a single-arm two-electrode blood pressure measuring method according to an embodiment of the disclosure.

FIG. 9 is a flowchart of a single-arm two-electrode blood pressure measuring method according to an embodiment of the disclosure. In Step S310, two sensing electrodes 110 are provided to sense an ECG signal of a user. Specifically, the two sensing electrodes 110 contact and are placed on the skin of an upper arm portion 200 of the user to obtain the ECG signal. Then, in Step S320, a PPG sensor 120 is provided to sense an PPG signal of the user. Next, proceed to Step S330, which is to perform an analysis of feature points according to the measured ECG signal and PPG signal, and calculate a first set of feature parameters; and proceed to Step S340, which is to generate a correction coefficient set by regression analysis according to multiple reference blood pressure values of the user and the first set of feature parameters, wherein the reference blood pressure value is obtained by the user measuring using a general household sphygmomanometer or by the user inputting according to a normal blood pressure range and includes systolic blood pressure and diastolic blood pressure. Next, proceed to Step S350, which is to detect the ECG signal and the PPG signal of the user, and also perform the analysis of the feature points to obtain a second set of feature parameters. Finally, proceed to Step S360, which is to substitute the second set of feature parameters and the correction coefficient set into a polynomial equation to calculate an estimated blood pressure of the user.

In another embodiment, the polynomial used in the disclosure may also be any of the following Equation (2), Equation (3), and Equation (4):

$$BP = a \cdot PAT + b \cdot HR + c \quad (2)$$

$$BP = a \cdot PAT + b \cdot HR + c \cdot PPI + d \quad (3)$$

$$BP = a \cdot PAT + b \cdot HR + c \cdot PW + d \quad (4)$$

Figure 10:
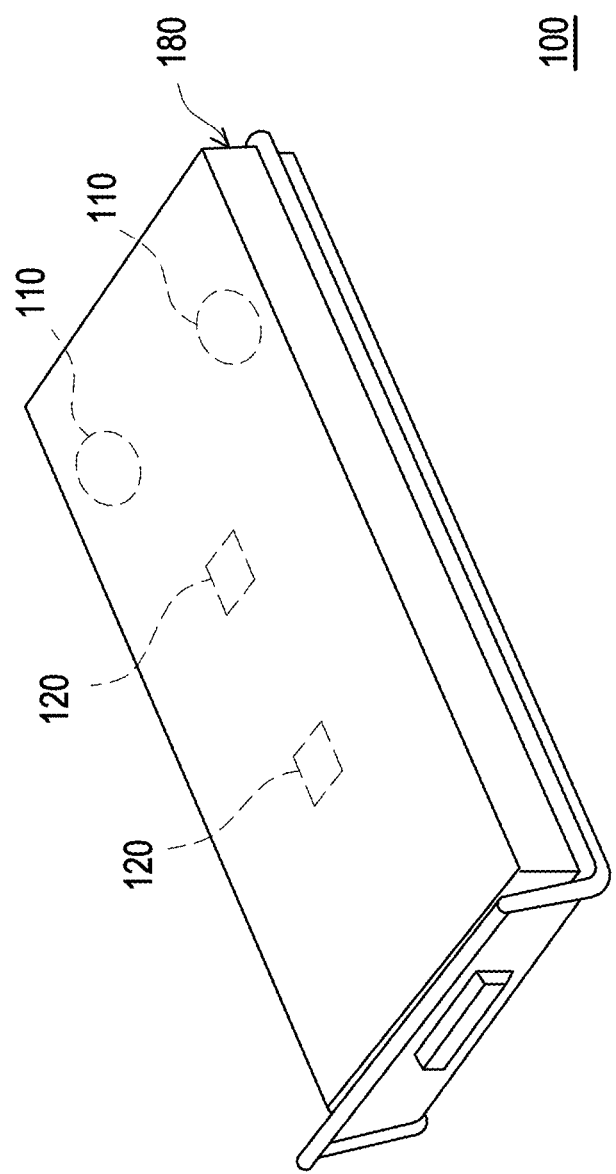
FIG. 10 is a three-dimensional schematic diagram of a single-arm two-electrode blood pressure measuring device according to another embodiment of the disclosure.

In an embodiment, the single-arm two-electrode blood pressure measuring device 100 further includes a fixing unit 180. The fixing unit 180 is connected to the two sensing electrodes 110, the PPG sensor 120, the analog signal processing unit 130, the analog-to-digital conversion unit 140, the digital signal processing unit 150, and the filter and amplifier unit 160. Specifically, the two sensing electrodes 110 and the PPG sensor 120 are disposed on the fixing unit 180. In addition, the two sensing electrodes 110 and a sensing electrode and/or a light receiving terminal of the PPG sensor 120 are exposed on a surface of the fixing unit 180 to contact the upper arm portion 200 of the user. It can be seen from FIG. 1 that in the embodiment, the fixing unit 180 is a strap and is configured to be disposed on a single arm of the user. FIG. 10 is a three-dimensional schematic diagram of a single-arm two-electrode blood pressure measuring device 100 according to another embodiment of the disclosure. As shown in FIG. 10, in the embodiment, the fixing unit 180 is a buckle base and is configured to buckle onto an armband. In another embodiment, the fixing unit 180 may also have an adhesive design and is configured to surround the one-arm two-electrode blood pressure measuring device 100 on an upper arm of the user and fix on the arm by adhering the head and the tail to each other, but the disclosure is not limited thereto. In other words, the single-arm two-electrode blood pressure measuring device 100 is fixed to the upper arm portion 200 of the user by the fixing unit 180, thereby improving the convenience of the single-arm two-electrode blood pressure measuring device 100 when in use.

The analog signal processing unit 130 and the digital signal processing unit 150 shown in FIG. 2 of the disclosure are, for example, central processing units (CPUs), other programmable general-purpose or specific-purpose micro control units (MCUs), microprocessors, graphics processing units (GPUs), image signal processors (ISPs), image processing units (IPUs), arithmetic logic units (ALUs), complex programmable logic devices (CPLDs), physics processing units (PPUs), programmable microprocessors, embedded control chips, digital signal processors (DSPs), application specific integrated circuits (ASICs), field programmable gate arrays (FPGAs), other similar elements, or a combination of the above elements.

In an embodiment, the single-arm two-electrode blood pressure measuring device 100 further includes a storage device, and the storage device is, for example, any type of fixed or removable random access memory (RAM), read-only memory (ROM), flash memory, hard disk, other similar devices, or a combination of the devices. The storage device stores multiple code snippets, multiple parameter definition values, correction models, multiple estimated blood pressure values, multiple reference blood pressure values, and multiple correction coefficients. After the code snippets or the correction models are installed, the code snippets or the correction models are executed by the analog signal processing unit 130 and the digital signal processing unit 150 to implement the single-arm two-electrode blood pressure measuring method of the disclosure.

The polynomial equation used in FIG. 6 of the disclosure may also be trained through an algorithm, which may be any of the following: supervised learning algorithm, support vector machine (SVM), logistic regression, random forest, artificial neural network (ANN), naïve Bayes classifier, decision tree, k-nearest neighbors, linear regression, relevance vector machine (RVM), perceptron, or other learning algorithms with similar objectives. The disclosure should not be limited thereto.

In summary, in the single-arm two-electrode blood pressure measuring device 100 of the disclosure, the filter 131 and the differential amplifier 132 of the analog signal processing unit 130 are used to invert amplify the common mode signal in the signal to serve as the reference voltage of the filter 131, thereby suppressing noise. In addition, the filter and amplifier unit 160 is combined to increase the signal-to-noise ratio of the PPG signal, while avoiding the aliasing phenomenon caused by high-frequency noise during sampling. It is worth noting that the single-arm two-electrode blood pressure measuring device 100 of the disclosure can continuously measure the blood pressure of the user and improves the disadvantage that an existing blood pressure measuring device must be contacted by both hands at the same time.

What is claimed is:

1. A single-arm two-electrode blood pressure measuring device, comprising:
    two sensing electrodes, configured to be placed on an upper arm portion of a user to obtain an electrocardiography (ECG) of the user;
    a photoplethysmogram (PPG) sensor, configured to be placed on the upper arm portion of the user to sense a PPG signal of the user;
    an analog signal processing unit, comprising a filter and a differential amplifier, wherein the filter is coupled to the two sensing electrodes, the differential amplifier is coupled to the filter, and inverts a common mode signal between the two sensing electrodes and then output to the filter, wherein the common mode signal, which is inverted, serves as a reference voltage of the filter, wherein the analog signal processing unit further comprises an integrator coupled to the differential amplifier and configured to remove an alternating current component of an electrical signal after passing through the differential amplifier and input to the differential amplifier as a reference voltage of the differential amplifier;
    a filter and amplifier unit, coupled to the PPG sensor and the differential amplifier, and configured to filter and amplify the ECG signal and the PPG signal;
    an analog-to-digital conversion unit, coupled to the filter and amplifier unit and configured to convert the ECG signal and the PPG signal from an analog format to a digital format; and
    a digital signal processing unit, coupled to the analog-to-digital conversion unit and configured to calculate a plurality of feature parameters of the ECG signal and the PPG signal to generate an estimated blood pressure value;
    wherein the digital signal processing unit comprises a calculation model, which is configured to calculate the feature parameters, wherein the feature parameters are divided into a first set of feature parameters and a second set of feature parameters; the digital signal processing unit generates a correction coefficient set by regression analysis according to a plurality of reference blood pressure values and the first set of feature parameters of the user, thereby continuously calculating an estimated blood pressure value of the user according to the correction coefficient set and the second set of feature parameters,
    wherein the correction coefficient set comprises a first coefficient corresponding to a pulse wave arrival time, a second coefficient corresponding to a heart rate, and a constant coefficient.

2. The single-arm two-electrode blood pressure measuring device according to claim 1, further comprising a fixing unit configured to fix the two sensing electrodes, the PPG sensor, the analog signal processing unit, the filter and amplifier unit, the analog-to-digital conversion unit, and the digital signal processing unit on the upper arm portion of the user.

3. The single-arm two-electrode blood pressure measuring device according to claim 2, wherein the fixing unit is an elastic armband.

4. The single-arm two-electrode blood pressure measuring device according to claim 2, wherein the fixing unit comprises a buckle base and an armband, and the buckle base is buckled onto the armband.

5. The single-arm two-electrode blood pressure measuring device according to claim 1, wherein the filter and amplifier unit further comprises a band pass filter, a first low pass filter, an offset adjuster, and a second low pass filter.

6. The single-arm two-electrode blood pressure measuring device according to claim 1, wherein the feature parameters comprise at least two of the pulse wave arrival time, a pulse-to-pulse interval, a pulse width, and the heart rate.

7. The single-arm two-electrode blood pressure measuring device according to claim 1, wherein the first set of feature parameters and the second set of feature parameters comprise at least one pulse wave arrival time and at least one heart rate.

8. The single-arm two-electrode blood pressure measuring device according to claim 7, wherein the first set of feature parameters and the second set of feature parameters further comprise at least one pulse-to-pulse interval, and the correction coefficient set further comprises a third coefficient corresponding to the pulse-to-pulse interval.

9. The single-arm two-electrode blood pressure measuring device according to claim 8, wherein the first set of feature parameters and the second set of feature parameters further comprise at least one pulse width, and the correction coefficient set further comprises a fourth coefficient corresponding to the pulse width.

10. A single-arm two-electrode blood pressure measuring method, comprising:
    providing two sensing electrodes to sense an ECG signal of a user;
    providing a PPG sensor to sense a PPG signal of the user;
    inverting a common mode signal between the two sensing electrodes and outputting to a filter by a differential amplifier, wherein the common mode signal, which is inverted, serves as a reference voltage of the filter;
    removing an alternating current component of an electrical signal after passing through the differential amplifier and inputting to the differential amplifier as a reference voltage of the differential amplifier;
    filtering and amplifying the ECG signal and the PPG signal by a filter and amplifier unit; and
    converting the ECG signal and the PPG signal from an analog format to a digital format by an analog-to-digital conversion unit;
    detecting a plurality of feature parameters of the ECG signal and the PPG signal by a digital signal processing unit, wherein the feature parameters are divided into a first set of feature parameters and a second set of feature parameters;

generating a correction coefficient set by regression analysis according to a plurality of reference blood pressure values and the first set of feature parameters of the user; and calculating an estimated blood pressure value of the user according to the correction coefficient set and the second set of feature parameters, wherein the correction coefficient set comprises a first coefficient corresponding to a pulse wave arrival time, a second coefficient corresponding to a heart rate, and a constant coefficient.

11. The single-arm two-electrode blood pressure measuring method according to claim 10, wherein the feature parameters comprise at least two of the pulse wave arrival time, a pulse-to-pulse interval, a pulse width, and the heart rate.

12. The single-arm two-electrode blood pressure measuring method according to claim 10, wherein the first set of feature parameters and the second set of feature parameters comprise at least one pulse wave arrival time and at least one heart rate.

13. The single-arm two-electrode blood pressure measuring method according to claim 12, wherein the first set of feature parameters and the second set of feature parameters further comprise at least one pulse-to-pulse interval, and the correction coefficient set further comprises a third coefficient corresponding to the pulse-to-pulse interval.

14. The single-arm two-electrode blood pressure measuring method according to claim 13, wherein the first set of feature parameters and the second set of feature parameters further comprise at least one pulse width, and the correction coefficient set further comprises a fourth coefficient corresponding to the pulse width.

15. A single-arm two-electrode blood pressure measuring method, comprising:

providing two sensing electrodes to sense an ECG signal of a user;

providing a PPG sensor to sense a PPG signal of the user;

inverting a common mode signal between the two sensing electrodes and outputting to a filter by a differential amplifier, wherein the inverted common mode signal serves as a reference voltage of the filter;

removing an alternating current component of an electrical signal after passing through the differential amplifier and inputting to the differential amplifier as a reference voltage of the differential amplifier;

filtering and amplifying the ECG signal and the PPG signal by a filter and amplifier unit; and converting the ECG signal and the PPG signal from an analog format to a digital format by an analog-to-digital conversion unit;

detecting a plurality of feature parameters of the ECG signal and the PPG signal by a digital signal processing unit, wherein the feature parameters are divided into a first set of feature parameters and a second set of feature parameters;

generating a correction coefficient set by regression analysis according to a plurality of reference blood pressure values and the first set of feature parameters of the user; and calculating an estimated blood pressure value of the user according to the correction coefficient set and the second set of feature parameters, calculating the feature parameters by the digital signal processing unit, dividing the feature parameters into the first set of feature parameters and the second set of feature parameters, wherein the first set of feature parameters and the second set of feature parameters comprise at least one pulse wave arrival time and at least one heart rate, and the correction coefficient set comprises a first coefficient corresponding to the pulse wave arrival time, a second coefficient corresponding to the heart rate, and a constant coefficient.

16. The single-arm two-electrode blood pressure measuring method according to claim 15, wherein the first set of feature parameters and the second set of feature parameters further comprise at least one pulse-to-pulse interval, and the correction coefficient set further comprises a third coefficient corresponding to the pulse-to-pulse interval.

17. The single-arm two-electrode blood pressure measuring method according to claim 16, wherein the first set of feature parameters and the second set of feature parameters further comprise at least one pulse width, and the correction coefficient set further comprises a fourth coefficient corresponding to the pulse width.

* * * * *